(12) United States Patent
Tripodi et al.

(10) Patent No.: US 9,821,269 B2
(45) Date of Patent: Nov. 21, 2017

(54) METHOD AND SYSTEM FOR MIXING GAS AND LIQUID FOR GRAVITATIONAL, PHYSICAL AND CHEMICAL COLLECTION OF COMPOUNDS

(71) Applicants: Innovation in Sciences & Technologies S.r.l., Rome (IT); Mauro Tripodi, Rome (IT); Paolo Tripodi, Rome (IT); Giuseppe Spanto, Rome (IT)

(72) Inventors: Mauro Tripodi, Rome (IT); Paolo Tripodi, Rome (IT)

(73) Assignees: IS Clean Air Italia S.r.l., Rovereto (TN) (IT); Mauro Tripodi, Rome (IT); Paolo Tripodi, Rome (IT); Giuseppe Spanto, Rome (IT)

( * ) Notice: Subject to any disclaimer, the term of this patent is extended or adjusted under 35 U.S.C. 154(b) by 0 days.

(21) Appl. No.: 14/441,042

(22) PCT Filed: Nov. 6, 2013

(86) PCT No.: PCT/IB2013/059954
§ 371 (c)(1),
(2) Date: May 6, 2015

(87) PCT Pub. No.: WO2014/072922
PCT Pub. Date: May 15, 2014

(65) Prior Publication Data
US 2015/0265966 A1    Sep. 24, 2015

Related U.S. Application Data

(60) Provisional application No. 61/722,932, filed on Nov. 6, 2012.

(30) Foreign Application Priority Data

Nov. 6, 2012    (IT) .............................. MI2012A1893

(51) Int. Cl.
*B01D 53/02*    (2006.01)
*B01D 53/14*    (2006.01)
(Continued)

(52) U.S. Cl.
CPC ................ *B01D 53/78* (2013.01); *A61L 9/20* (2013.01); *B01D 47/06* (2013.01); *B01D 53/14* (2013.01); *B01D 53/1406* (2013.01); *B01D 53/38* (2013.01)

(58) Field of Classification Search
CPC ............ B01D 2258/0291; B01D 53/78; B01D 53/77; B01D 53/38; B01D 53/34; B01D 53/14; B01D 53/02
See application file for complete search history.

(56) References Cited

U.S. PATENT DOCUMENTS 2,539,992 A    1/1951    Cover
2,785,962 A    3/1957    Ruth
(Continued)

FOREIGN PATENT DOCUMENTS

DE    196 36 434 A1    3/1997
EP    1 398 066 A2    3/2004
(Continued)

OTHER PUBLICATIONS

International Search Report issued in connection with PCT/IB2013/059954, dated Mar. 18, 2014.
(Continued)

*Primary Examiner* — Timothy Vanoy
(74) *Attorney, Agent, or Firm* — Akerman LLP (57) ABSTRACT

A method is described for mixing gas and liquid for gravitational, physical and chemical collection of compounds or particles, based on decreasing of the compounds free mean path in a vessel, and comprising the steps of: gravitational depletion, involving abating compounds and liquid chemical solution drops with higher diameter than higher volume; physical deposition, involving the condensation of abated compounds on a wet surface of the vessel; chemical adsorp- (Continued)

tion, involving chemical reaction between the abated compounds and the species in the liquid chemical solution.

17 Claims, 5 Drawing Sheets

(51) Int. Cl.
    *B01D 53/34*     (2006.01)
    *B01D 53/77*     (2006.01)
    *B01D 53/78*     (2006.01)
    *B01D 47/06*     (2006.01)
    *A61L 9/20*     (2006.01)
    *B01D 53/38*     (2006.01)

(56) References Cited

U.S. PATENT DOCUMENTS

| | | |
|---|---|---|
| 3,105,103 A | 9/1963 | Old |
| 3,321,191 A | 5/1967 | Najarian |
| 3,378,241 A | 4/1968 | Stokes |
| 3,885,929 A | 5/1975 | Lyon et al. |
| 4,623,523 A | 11/1986 | Abrams et al. |
| 5,308,385 A | 5/1994 | Winn |
| 7,214,349 B2 * | 5/2007 | Holst ............ B01D 47/06 422/168 |
| 2006/0107833 A1 | 5/2006 | Thundyil et al. |

FOREIGN PATENT DOCUMENTS

| | | | |
|---|---|---|---|
| GB | 1403147 A * | 8/1975 | ............ B01D 47/06 |
| WO | 2008/053871 A1 | 5/2008 | |

OTHER PUBLICATIONS

Italian Search Report issued in connection with Application No. MI2012A001893, dated May 27, 2014.

* cited by examiner

METHOD AND SYSTEM FOR MIXING GAS AND LIQUID FOR GRAVITATIONAL, PHYSICAL AND CHEMICAL COLLECTION OF COMPOUNDS

This application is a national phase of PCT/IB2013/059954, filed Nov. 6, 2013, and claims priority to Italian Patent Application No. MI2012A001893, filed Nov. 6, 2012, and U.S. Provisional Application No. 61/722,932, filed Nov. 6, 2012, the entire contents of which are hereby incorporated by reference.

FIELD OF THE INVENTION

The present invention relates to a method and system, that mix gas and liquid streams to collect, in the liquid stream, the chemical compounds present in the fluid stream, and in particular for mixing gas and liquid for gravitational, physical and chemical collection of compounds.

DESCRIPTION OF THE PRIOR ART

It is known that the influence of daily human life onto environment raises problems in every field. One of the problems is generation of pollutants caused by industrial plant, transportation, residential and agricultural activity including farming, air pollution in general.

For example, an exhaust gas exhausted from municipal waste incinerators contains particulate matter, $O_3$, HCl, $SO_x$, $NO_x$, heavy metals including mercury, or minor constituents such as dioxin, furan, and it is necessary to remove these toxic substances from a viewpoint of environmental protection. Other substances like $CH_4$, $C_6H_6$ and PAH's are emitted in atmosphere. It is known that some of these substances are remarkably high in toxicity and further have carcinogen effects, and trapping/collecting/removing these dioxins is considered an urgent problem.

Another example is the problem raised for worker's health protection in industrial areas, due to their breathing dust from fiberglass, asbestos, wood, marble, etc.

SUMMARY OF THE INVENTION

Therefore it is the main object of the present invention to propose a method and system for mixing gas and liquid for gravitational, physical and chemical collection of compounds able to solve the above described problems.

It is a particular object of the present invention a method for mixing gas and liquid for gravitational, physical and chemical collection of compounds or particles in a vessel, and comprising the steps of:
 gravitational depletion, involving abating compounds or particles and liquid chemical solution drops with greater diameter and greater volume than the diameter and volume of said compounds or particles;
 physical deposition, involving the condensation of abated compounds on a wet surface of the vessel;
 chemical adsorption, involving chemical reaction between the abated compounds and the species in the liquid chemical solution,
so as to decrease the free mean path of said compounds or particles in the vessel.

Preferably the method comprises the steps of:
 entering the gas into a separation chamber in the vessel through gas inlets, in the vessel a liquid solution bath being present;
 in the separation chamber mixing the gas stream with a liquid solution stream in-flow, becoming a fluid stream so that:
 some of compounds or particles are deposited on the separation chamber walls and then washed out to the liquid solution bath;
 some other compounds or particles are adsorbed in chemical solution drops and then collected in the liquid solution bath;
 some other compounds or particles are collapsed through diverting surfaces and washed out;
 remaining compounds or particles follow the liquid solution stream going to the bottom of the vessel and then rising, in a non-laminar flow, to a separator bed inside a mixing chamber of the vessel where the fluid is mixed in counter-flow with the flow of sprayed liquid chemical solution, so that all the already wet compounds or particles are absorbed by said flow and forced gravitationally to fall in the liquid bath;
 exiting the fluid stream from the vessel after separation of said compounds or particles.

It is a further object of the present invention a system adapted for mixing gas and liquid for gravitational, physical and chemical collection of compounds or particles in a vessel, comprising the following elements:
 a gravitational depletion unit, configured for abating compounds and liquid chemical solution drops with greater diameter and greater volume than the diameter and volume of said compounds or particles;
 a physical deposition unit, configured for the condensation of abated compounds on a wet surface of the vessel;
 a chemical adsorption unit, configured for chemical reaction between the abated compounds and the species in the liquid chemical solution,
so as to decrease the free mean path of said compounds or particles in the vessel.

Preferably the system comprises:
 said vessel adapted to contain said liquid and comprising a mixing volume of said gas and liquid above the surface of said liquid,
 a number of gas loading conduits connected to corresponding saturation chambers, loading said fluid stream into the mixing volume, the internal walls of said saturation chambers behaving as a first gas to liquid exchange surface;
 at least a conduit for fluid discharge to the outside of the vessel after mixing,
 at least a distributor of said liquid with a number of sprayers, adapted to spray said liquid in said mixing volume and in said saturation chambers;
 at least a diverter placed at corresponding saturation chamber ends, said diverter forcing the fluid stream to go in the bottom part of the vessel and behaving as a second fluid to liquid exchange surface, as a catalytic surface.

These and further objects are achieved by means of a method and system for mixing gas and liquid for gravitational, physical and chemical collection of compounds, as described in the attached claims, which form an integral part of the present description.

BRIEF DESCRIPTION OF THE DRAWINGS

The invention will become fully clear from the following detailed description, given by way of a mere exemplifying and non limiting example, to be read with reference to the attached drawing figures, wherein.

The same reference numerals and letters in the figures designate the same or functionally equivalent parts.

DETAILED DESCRIPTION OF THE PREFERRED EMBODIMENTS

The general principles of the method for mixing gas and liquid for gravitational, physical and chemical collection of compound, subject of the invention are the following.

The method is based on decreasing of the compounds free mean path using gravitational depletion, physical deposition and chemical adsorption, in a vessel.

The first mechanism (gravitational depletion) involves abating compounds and the liquid chemical solution drops with higher diameter than higher volume (big drops mean larger volume of liquid drop).

The second mechanism (physical deposition) involves the condensation of abated compound on the large wet surface of the system.

The third mechanism (chemical adsorption) involves chemical reaction between the abated compound and the species in the liquid chemical solution.

An example of embodiment of the method will be described afterwards.

For the embodiment of the method a system is provided, for mixing gas and liquid for gravitational, physical and chemical collection of compounds, based on the decreasing of compounds free mean path in a vessel, comprising the following elements:

a gravitational depletion unit, involving abating compounds and liquid chemical solution drops with higher diameter than higher volume;

a physical deposition unit, involving the condensation of abated compounds on a wet surface of the vessel;

a chemical adsorption unit, involving chemical reaction between the abated compounds and the species in the liquid chemical solution.

In the following an example of embodiment of the system of the invention is described with reference to the enclosed figures.

Figure 1:
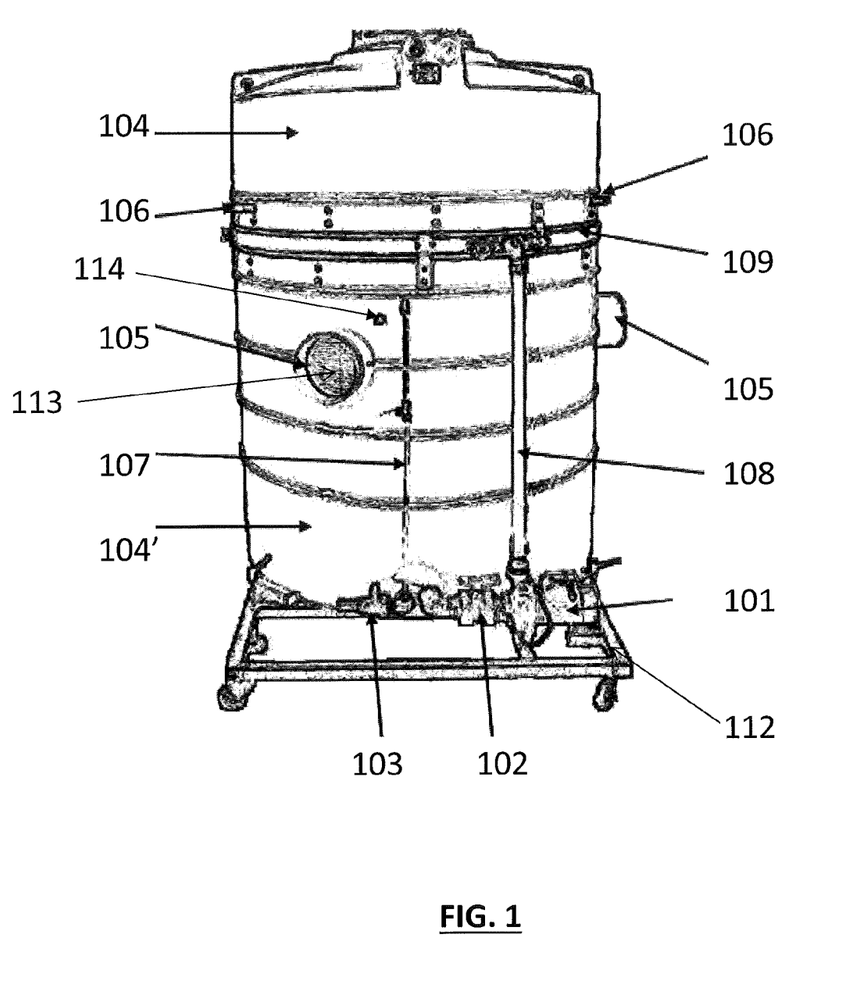
FIG. 1 shows an example of embodiment of a vessel in accordance with the invention.

First of all the system comprises a vessel as in FIG. 1.

The vessel is adapted to contain the liquid used for the liquid stream in the process, as described below. Vessel can be placed on a wheel's platform 112 for positioning and ground leveling. Preferably handles 106 are present for managing the movement of the vessel.

The vessel can have cylindrical geometry or cubic or parallelepiped or custom geometry. Volumetric dimension depends on the gas stream volume to be treated.

The vessel material can be polymer like polyethylene, metallic like steel, fiberglass and other stable material not dangerous for the environment and biological life. The material is chosen with respect to the use and the type of liquids and gas used.

The vessel is provided with a connector for liquid drainage 103 (diameter greater than half inch), a connector for liquid picks 102 (diameter greater than half inch) and a connector for liquid loading 114 (diameter greater than half inch).

The vessel contains a liquid chemical solution in the bottom part 104', and preferably a floating surface, and/or a floating polymeric net, and/or floating spheres having many diameters, covering the liquid chemical solution's surface.

An external tube 107 can be present for showing the liquid level in the vessel.

These bodies are floating in the vessel and are suited for increase the fluid-liquid contact surface and, depending on the field, decreasing of liquid chemical solution evaporation, like water.

The vessel is provided with a number of conduits 105 in the lateral sides of the vessel for gas loading inside the vessel, and at least one conduit 110 for fluid discharge to the outside of the vessel. The conduits can have circular, squared, rectangular, elliptical and custom section. The number of such conduits can reach 6 in any one vessel. The inlet fluid loading pressure in the vessel is less than 10 bar.

The conduits contain gas flow sensors, temperature and relative humidity sensors.

The conduits are safeguarded with a net 113 to avoid the intrusion inside the vessel.

The net can be made in metal like steel, in polymer or in any material not dangerous for environment and biological life. The net has a mesh greater than 0.5 [mm].

Figure 4:
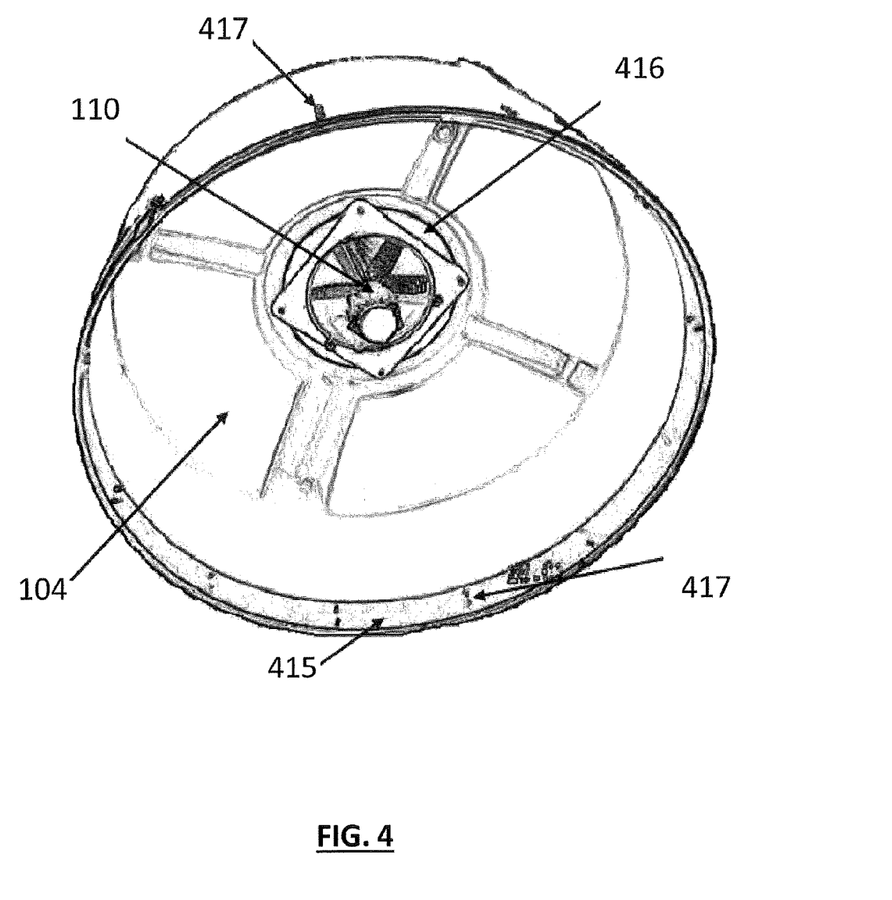
FIG. 4 shows example of embodiment of a Fan System component of the vessel.

The vessel contains an aspirator 110, preferably a fan, forcing the fluid stream to go out of the vessel through it. The fan creates a depression inside the vessel favoring the inlet inside the vessel of external gas (air) through the conduits 105.

The fan has variable angular speed, it contains electrical voltage and current sensors, fluid flow sensors temperature and relative humidity sensors.

Figure 2:
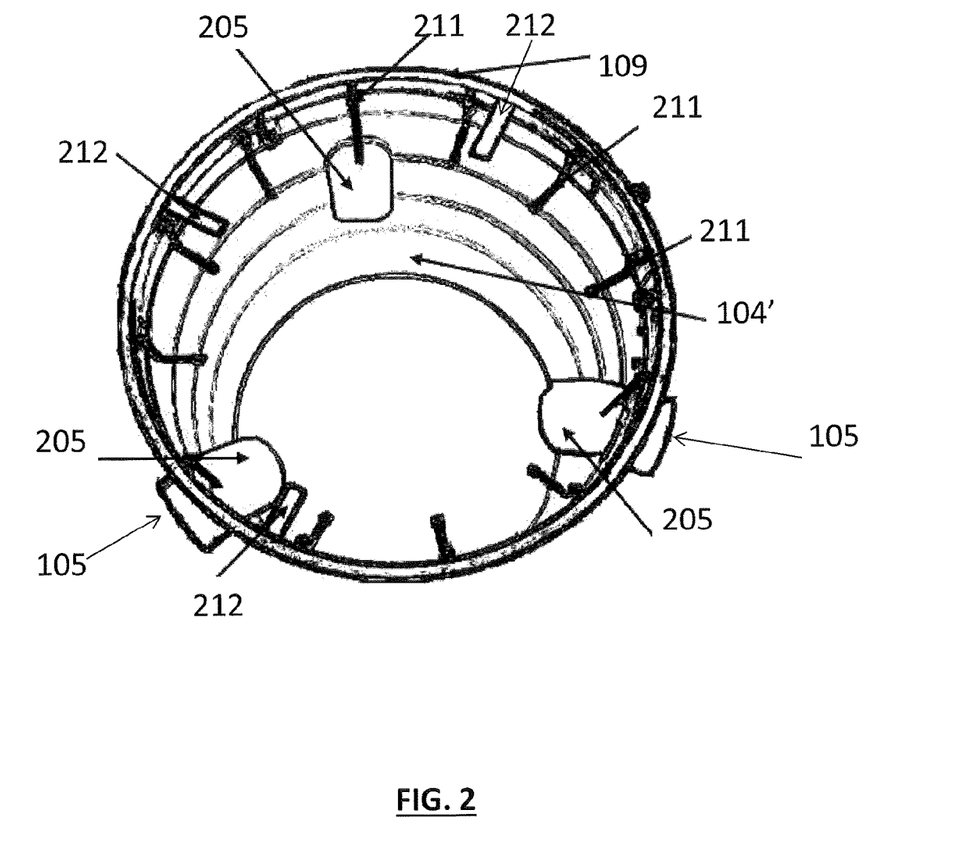
FIG. 2 shows example of embodiment of Manifold, Sprayer, Saturation Chamber, components of the vessel.

With reference to FIGS. 1 and 2, the vessel shows an upper part 104 and a bottom part 104'. Between them at least a distributor of liquid solution, i.e. a manifold 109 is present in an intermediate position above the surface of the liquid solution, and placed around the circumference of the vessel, particularly around the perimeter of the vessel depending on shape.

A closed liquid solution pumping system is present in the vessel, comprising a pump 101, a charge tube 108 for the liquid solution to flow from the bottom part of the vessel 104' to the manifold 109, and from the manifold to the inside of the vessel. A charge connector and valve 102 and a discharge connector and valve 103 for the liquid solution are present to the outside of the vessel.

A number of tubes with sprayer 211 are symmetrically distributed on the manifold, the distribution can be even asymmetrical depending on the number of conduits 105.

The pump contains electrical voltage and current sensors, and the hydraulic tubes contains liquid flow sensors.

The liquid is counter-flow and in-flow sprayed with respect to the fluid flow respectively in a number of saturation chambers 205 connected to the conduits 105 for gas loading (FIG. 2, 3), and in the mixing volume inside the vessel. The mixing volume is the volume where the fluid is, and is delimited laterally by the vessel surface, on the bottom by the floating surface on the liquid chemical solution surface, on the top by the packed bed surface (described below).

Figure 3:
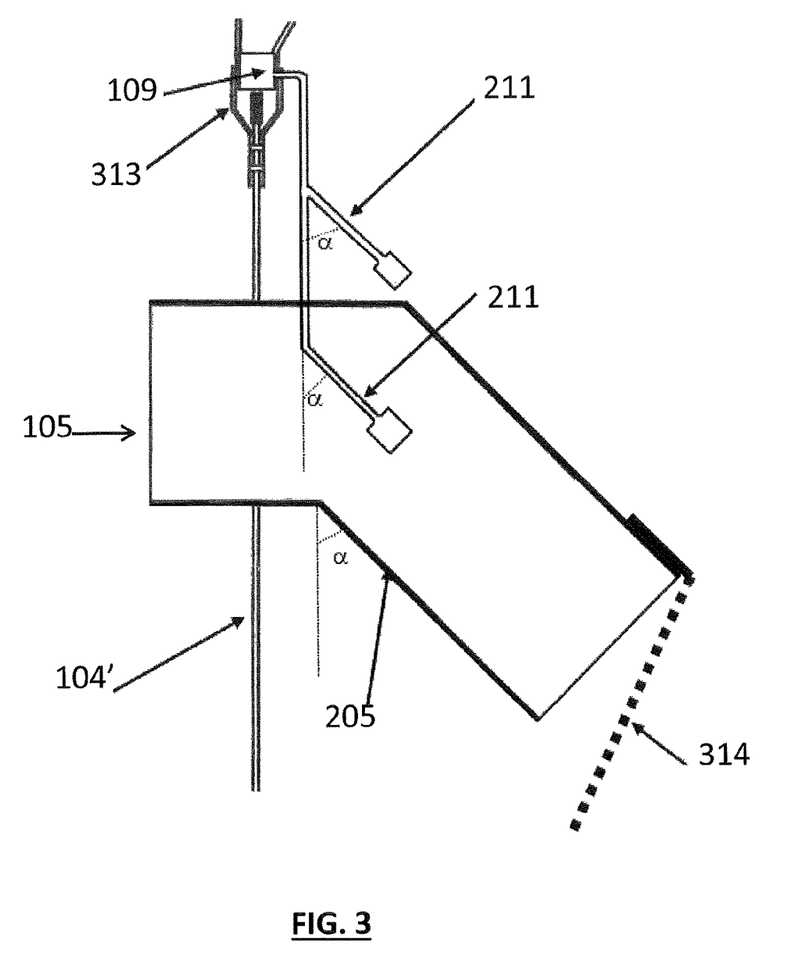
FIG. 3 shows example of embodiment of a Sprayer System component of the vessel.

The conduits and saturation chambers 105, 205 are preferably curved downside with an angle α in the range 0-90 degree, preferably α in the range 30-60 degree, preferably α=45°.

Sprayers 211 (FIG. 3) spray the liquid solution from the manifold 109 to both inside the saturation chambers 205 and outside the conduits inside the vessel in the mixing volume.

The sprayers 211 produce liquid jet with a large range of liquid drop diameter, preferably greater than 0.1 μm.

The liquid drop shape goes from spherical to elliptical.

The spray shape is full conic, hollow conic, flat jet, the spray angle is in the range 15-100 degree, preferably in the range 80-100 degree, preferably 90 degree.

In order to keep clean the sprayers, piezoelectric components (not shown in the figures) are mechanically in perfect contact with the sprayers. Periodically, preferably with a frequency greater than 3 mHz, an appropriate electronic control system excites all the present piezoelectric elements for a time period greater than 100 ms.

Growth of contaminant deposition is not allowed with this procedure.

Figure 5:
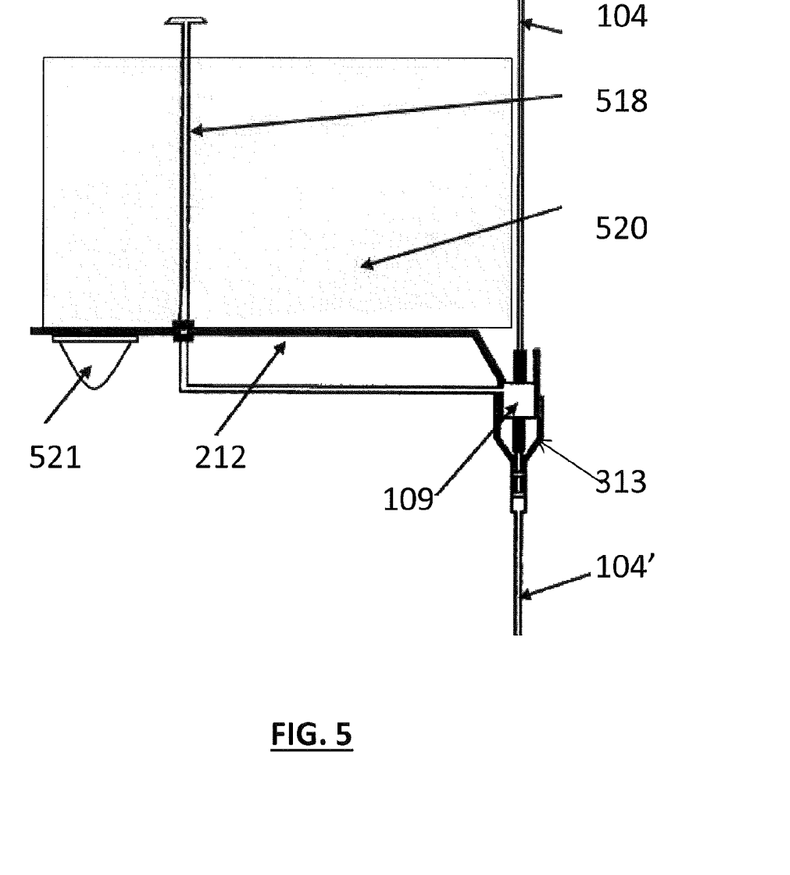
FIG. 5 shows example of embodiment of Separator/Demister Washing System and UV System components of the vessel.

A number of holders 212 for a corresponding number of separator/demister washing systems are present at the internal walls of the vessel, as described below with reference to FIG. 5.

The conduits 105-205 for gas stream loading are working like a saturation chamber.

As said above, the tube with sprayer 211 inside the conduit is present in order to wet all the surface of the conduit, release sprayed liquid stream in all the conduit volume inflow with gas stream, producing a fluid stream.

At the conduit/saturation chamber end, a diverter 314 is present: the sprayed liquid wets the diverter where it is stopped.

Saturation chamber internal walls represent the first gas to liquid exchange surface.

The saturation chamber contains gas flow sensors and temperature and relative humidity sensors.

As apparent from FIG. 3, the diverter 314 is used to change the fluid stream direction. The diverter forces the fluid stream to go in the bottom part of the vessel.

The diverter is the second gas to liquid exchange surface and is a stopper for the larger particle compounds present in the fluid stream. The diverter has a geometry depending on the flow parameters; the diverter profile can be parabolic, elliptic, circular, linear or a combination of profiles.

Preferably the materials used for the diverter 314 are metals, polymer and any material not dangerous for environmental and biological life. The diverter surface material depends on the catalytic process that are involved.

The diverter behaves like a catalytic surface.

In addition some manifold holders 313 can be present on the upper circumference of the bottom side of the vessel.

With reference to FIG. 4, the fan system 110 is present in the upper side of the vessel. As said above, the fan system provides the fluid stream flow.

Preferably the flux must be greater than 10 [$m^3h^{-1}$], and the pressure drop must be greater than 50 Pa inside the vessel.

The fan electrical insulation is made in order to work even in explosive atmosphere environment, according to the ATEX (ATmosphères ed EXplosibles) standard, according to the Directive 94/9/CE.

For closing the two parts of the vessel together, tight bolts and nuts 417 and a reinforcing and sealing band 415 are present around the boundaries. A gasket 416 surrounds the fan.

In some cases, the system can treat gas, liquid, fluid containing bacteria, spores and in general microbiologic species.

To avoid contamination and deplete the microbiological charge, a microbiological treatment is made to the fluid (gas plus liquid) inside the vessel; preferably an UV-light system is installed where the fluid is formed.

As described in FIG. 5, an UV Lamp system 521 is present connected to an holding structure 212 for a separator/demister 520; the holding structure 212 is connected to the side wall of the vessel. In addition a separator/demister washing tube and sprayer 518 is present, picking up liquid solution from the manifold 109 and spraying it on the separator/demister 520, which can be placed above the manifold.

Separator and mist eliminator, specifically named packed bed, is shown in FIG. 5. In chemical processing this is normally a hollow tube, pipe, or other vessel that is filled with a packing material. The packing can be randomly filled with small objects like raschig rings, circular disks, spherical or cylindrical bodies, or otherwise it can be a specifically designed structured packing. Packed beds may also contain catalyst particles or adsorbents such as zeolite pellets, granular activated carbon, etc. The purpose of a packed bed is typically to improve contact between two phases in a chemical or similar process to extract specific compound from the fluid phase.

In the following an example of embodiment of the method for mixing gas and liquid for gravitational, physical and chemical collection of compounds of the invention is described, as performed in a vessel as described above.

In the fluid stream many undesired compounds or particles are present, for example let's consider asbestos particles with mean diameter of about 5 μm.

These particles enter the system through the gas inlet tube and passed the grid are inside the separation chamber.

In the separation chamber the gas stream is mixed with the liquid solution stream, producing the fluid stream; the two streams are in-flow: some of particles are deposited on the separation chamber wall and then washed out to the liquid solution bath, some others will be adsorbed in the chemical solution drops and then collected in the liquid solution bath, some others will collapse on the diverter surface and be washed out.

The remaining particles will follow the fluid stream going to the bottom of the vessel and then rising, in a non-laminar flow, to the separator bed inside the mixing chamber of the vessel where the fluid is mixed in counter-flow with intensive and dense flow of sprayed liquid chemical solution.

All the already wet particles that are absorbed by the large volume liquid solution drops are forced gravitationally to fall in the liquid bath.

Other particles are deposited on the vessel mixing chamber and then washed out.

Some particles increase the volume and weight because of the wetness and arrive to the separator. Here the separation surface is very large and the particles continue to condensate on the surfaces. The free mean path in here is strongly reduced.

To assure wetness onto the separator surface a washing system sprays liquid solution inside the separator. A very high percentage of particles in the fluid stream are removed from the stream and forced inside the bath.

The fluid stream flows out of from the system through the fluid outlet where the fan is situated.

Chemical reactions occur in the liquid bath and on the catalytic surface (like metal surface inside the vessel) inside the system between fluid species and liquid chemical species.

Liquid to Gas Ratio Ψ.

Important parameter of the system is the rate of liquid flow, in the manifold and tubes.

It is common in this system's terminology to express the liquid flow as a function of the gas flow rate that is being treated.

This is commonly called the liquid-to-gas ratio Ψ and uses the units of liquid per cubic meter [lm$^{-3}$].

Expressing the amount of liquid used as a ratio enables systems of different sizes to be readily compared.

Ψ is a function of the mechanical design of the system; while for gas absorption this ratio gives an indication of the difficulty of removing pollutant.

For particulate matter control, Ψ is preferably in the range of
0.3 to 3 [lm$^{-3}$].

Depending on systems design, a minimum volume of liquid is required to "wet" the internal exchange surface and create sufficient collection targets. Adding excess liquid to this systems does not affect efficiency and in fact, does not cause pressure loss.

Ψ for gas absorption are often higher, in the range of 3 to 6 [l/m$^{-3}$].

The particular embodiment of the system described above is developed to work with Ψ>0.5 [lm$^{-3}$].
with a liquid to fluid ratio preferably in the range of Ψ≤10 per [lm$^{-3}$], more preferably also Ψ>0.5 [lm$^{-3}$].

For example in a big town it can be Ψ=7.83 [lm$^{-3}$].

Dynamic Mass Stream Ratio Ξ.

The Ψ parameter is not the only significant parameter to describe the system, because design dependent. More significant is the mass of both streams (liquid and gas) that is correlated with density of liquid and gas used in the system and method.

In the following the relation that describes the working range for the systems is given. Given m the mass measured in [Kg], δ the density measured in [Kg m$^{-3}$] and V is the volume measured in [m$^3$], for the two streams we have:

$$m_{stream} = \delta_{stream} \cdot V_{stream}$$

The dynamics of the system led us to define the mass variation for both streams:

$$\frac{\partial m_{stream}}{\partial t} = \delta_{stream} \cdot \frac{\partial V_{stream}}{\partial t}$$

Then the system must follow the relationship:

$$\Xi = \frac{\frac{\partial m_{gas}}{\partial t}}{\frac{\partial m_{liquid}}{\partial t}} \leq 10$$

with a liquid to fluid ratio preferably in the range of Ψ≤10 per [lm$^{-3}$], more preferably also Ψ>0.5 [ exiting the fluid stream from the vessel after separation of said compounds or particles.

4. A system adapted for mixing gas and liquid for gravitational, physical and chemical collection of compounds or particles in a vessel, based on decreasing the free mean path of said compounds or particles in said vessel, comprising the following elements in said vessel:
spraying units of said liquid in-flow and in counter-flow with respect to the gas flow;
a gravitational depletion unit, involving abating compounds or particles and liquid chemical solution drops with greater diameter and greater volume than the diameter and volume of said compounds or particles;
a physical deposition unit, involving the condensation of abated compounds or particles on a wet surface of the vessel;
a chemical adsorption unit, involving chemical reaction between the abated compounds or particles and the species in the liquid chemical solution; and
floating surfaces covering said liquid chemical solution's surface, the floating surfaces selected from the group consisting of a floating polymeric net, floating spheres having various diameters and mixtures thereof.

5. The system as in claim 4, comprising:
said vessel adapted to contain said liquid and comprising a mixing volume of said gas and liquid above the surface of said liquid, producing a fluid stream,
a number of gas loading conduits connected to corresponding saturation chambers wherein a fluid stream is formed, loading said fluid into the mixing volume, the internal walls of said saturation chambers behaving as a first gas to liquid exchange surface;
at least a conduit for fluid discharge to the outside of the vessel after mixing,
at least a distributor of said liquid with a number of sprayers, adapted to spray said liquid in said mixing volume and in said saturation chambers;
at least a diverter placed at corresponding saturation chamber ends, said diverter forcing the fluid stream to go in the bottom part of the vessel and behaving as a second fluid to liquid exchange surface, as a catalytic surface.

6. The system as in claim 5, comprising:
one or more separator/demisters, inside the vessel above the at least a distributor, as packed beds for separating chemical compounds from said fluid; and
one or more UV Lamp system connected to corresponding separator/demisters.

7. The system as in claim 5, comprising floating bodies on said floating surfaces of the liquid inside the vessel, adapted to increasing the fluid-liquid contact surface, and decreasing the liquid chemical solution evaporation.

8. The system as in claim 5, wherein said at least a conduit for fluid discharge comprises an aspirator forcing the fluid stream to go out of the vessel through it.

9. The system as in claim 8, wherein said aspirator is adapted to create a fluid stream flux to go out of the vessel greater than 10 $m^3h^{-1}$, and a pressure drop greater than 50 Pa inside the vessel.

10. The system as in claim 5, comprising a pumping system adapted for the liquid to flow from the bottom part of the vessel to the distributor, and from the distributor to the inside of the vessel.

11. The system as in claim 5, wherein said loading conduits and saturation chambers are curved downside with an angle ($\alpha$) in the range of 0-90 degrees.

12. The system as in claim 11, wherein the angle ($\alpha$) of said loading conduits and saturation chambers is in the range of 30-60 degrees.

13. The system as in claim 12, wherein the angle ($\alpha$) of said loading conduits and saturation chambers is 45 degrees.

14. The system as in claim 5, wherein said number of sprayers produce liquid jet with a spray angle in the range 15-100 degrees.

15. The system as in claim 14, wherein the spray angle is in the range of 80-100 degrees.

16. The system as in claim 15, wherein the spray angle is 90 degrees.

17. The system as in claim 5, comprising piezoelectric components in contact with the sprayers adapted to keep the sprayers clean.

* * * * *